United States Patent [19]

Smith et al.

[11] Patent Number: 4,737,648

[45] Date of Patent: Apr. 12, 1988

[54] APPARATUS FOR DETECTING FIBROUS PARTICLE SIZES BY DETECTING SCATTERED LIGHT AT DIFFERENT ANGLES

[75] Inventors: Nigel P. Smith, Winsford; Neil A. Downie, Sale, both of England

[73] Assignee: VG Instruments Group Limited, England

[21] Appl. No.: 911,463

[22] Filed: Sep. 25, 1986

[30] Foreign Application Priority Data

Sep. 26, 1985 [GB] United Kingdom ............... 8523747

[51] Int. Cl.⁴ .................................................. G01N 21/86
[52] U.S. Cl. ........................................ 250/560; 356/343
[58] Field of Search ................. 250/560, 561; 356/335, 356/336, 339, 343; 340/627

[56] References Cited

U.S. PATENT DOCUMENTS 4,146,799  3/1979  Pitt et al. ........................... 356/343
4,284,355  8/1981  Hansen et al. ..................... 356/335
4,540,283  9/1985  Bachalo ............................. 356/336
4,672,216  6/1987  Pitt et al. ........................... 356/343

Primary Examiner—David C. Nelms
Assistant Examiner—Stephone B. Allen
Attorney, Agent, or Firm—Bacon & Thomas

[57] ABSTRACT

The invention comprises apparatus capable of unambiguous determination of the length and diameter of fibrous particles, especially asbestos fibres, based on near-forward scattering of light by fibres aligned in a hydrodynamically focused gas flow. Three portions of scattered light are detected, two portions perpendicular to the fibre axis and one aligned with it, from which length and diameter can be independently determined. This independence is achieved by allowing only selected parts of the light scattered within certain selected ranges of angles to reach each detector. A two-detector instrument capable of accurate determination of fibre diameter is also described.

23 Claims, 3 Drawing Sheets

APPARATUS FOR DETECTING FIBROUS PARTICLE SIZES BY DETECTING SCATTERED LIGHT AT DIFFERENT ANGLES

This invention relates to the determination by an optical method of the size of particles carried in a fluid flow, and especially to the determination of the size and fibrosity of asbestos particles in air.

The determination of the size of particles carried in a fluid, whether of biological cells, aerosol droplets, dust, or fibres such as asbestos, is of considerable industrial importance. Consequently a large number of methods based on a variety of techniques have been developed, between them capable of estimating particle sizes over a range of about seven orders of magnitude, and operable with particle concentrations ranging from a single particle to very heavily laden smokes and aerosols. Amongst the optical techniques, those based on the scattering of light (or other electromagnetic radiation) by one or more particles are well known, and many instruments utilizing the . technique are available commercially. The size range of particles which is of greatest interest is from 1–10 micron diameter, in which range the light scattering theory developed by Mie is applicable. A number of workers have shown that by measuring the intensity of scattered light at a particular angle to the incident beam, the size of the particle responsible for the scattering can be found. Rigorous application of the Mie theory does allow the particle size to be calculated without the need for calibration, but this requires a knowledge of the refractive index of the particles and the assumption that they are spherical. Further, since the absolute intensity of a single scattered beam is being measured, the instrument is sensitive to changes in the intensity of the light source, and another difficulty is caused by the use of a laser as a light source because the intensity distribution across its beam is not constant but has a Gaussian profile. Consequently, particles passing through the edges of the beam will scatter less light than if they pass through the centre, and will be classified as smaller than they actually are. In practice, instruments are usually calibrated with spherical particles of known diameter, so that any deviation from sphericity of the unknown particles can also yield incorrect results. Further, the theoretical relationship between the scattered light intensity and particle size is complex, and contains both regions where there are several particle sizes which result in the same scattered light intensity and regions where the scattered intensity is relatively insensitive to the particle size. The relationships are markedly different at different angles of scatter to the incident beam. It is found that the effects of microscopic particle irregularity and particle refractive index variation are least at scattering angles which are close to the direction of the primary beam, so that instruments which monitor the scattered light at a small angle to the path of the incident beam (typically 5°–20°) are in general preferred. Such an instrument, based on the near-forward scatter principle, has been described by Holve, D., and Self, S. A., in "Laser Velocimetry and particle sizing" edited by H. D. Thompson and W. H. Stevenson, published by Hemisphere Publication Corporation, Washington, 1979 at p. 397. However, instruments based on right angle scattering are also common, for example as described by Suda, K., in Review of Scientific Instruments, 1980, vol. 51, p. 1049, because the range of scattering intensity for 0.1–10 micron particles is least in this direction and construction of a high sensitivity instrument is facilitated.

J. R. Hodkinson (Applied Optics, 1966, vol. 5 p. 839) proposed that the problems of multivaluedness and of the sensitivity of the near-forward scatter Mie relationships to refractive index, and of the non-uniform intensity distribution of a laser light source, could be largely overcome by simultaneously measuring the scattered light at two different angles within the forward lobe, and determining the ratio of the intensities, which ratio could be related to the size of the scattering particles. Many instruments based on this principle have been constructed. The selection of the most suitable pair of angles is dependent on the range of sizes to be monitored, and Hirleman (Proc. Conf. Laser 77- Opto Electronics, Munich, June 1977, Publ. by IPC Science and Technology Press, p. 740) has described a multiple-ratio scattering instrument which is suited to monitoring a wide range of particle sizes and which maximizes the efficiency of detection by monitoring the light scattered in a series of hollow cones of different included angles by means of a detector comprising a series of concentric annular rings. A similar instrument is described by Diel, Smith and Sydar in Applied Optics, 1979, vol. 18, p. 1653.

Two further problems are inherent with instruments of this type. First, they are essentially single particle counters, that is, the scattering due to a single particle is measured to determine its size. Thus, if more than one particle is present in the sensing volume of the instrument at any instant, incorrect results will be obtained. A limit is therefore placed on the concentration of particles which can be monitored before the contribution of signals due to more than one particle becomes too great. Secondly, signals from particles passing through the edges of the sensing volume where the beam intensity is low must either be eliminated or corrected. One way of achieving this is to sample the fluid containing the particles and pass it through the instrument, constraining the flow into a narrow jet so that the particles are passed through the sensing volume in single file. This technique, known as hydrodynamic focusing, is utilized in an instrument described by Eisert, Ostertag and Nieman (Review of Scientific Instruments, 1975, volume 46 p. 1021). The concentration of particles can be reduced by adding a flow of clean fluid (typically the filtered fluid emerging from the sensing volume) to the input, usually in the form of a sheath around the particle containing stream, as described in U.S. Pat. No. 3,791,196.

In the case of fibrous particles, especially asbestos, instruments of the type described above are of limited use because they are capable of classifying particles only by one dimension, whilst medical evidence suggests that both the aspect ratio and the absolute size are significant in recognizing particles which are likely to endanger health. Use of these instruments to classify fibrous particles is likely to yield misleading results, because spherical particles of a certain size range, not likely to endanger health, will be classified alongside dangerous fibres, and more seriously, the presence of some dangerous fibres may be underestimated due to their passing through the sensing volume in a different orientation to that needed for them to give a positive signal.

Unlike the case of instruments suitable for spherical particle analysis, the number of instruments suitable for fibre size analysis is limited. Conventional scattering instruments utilizing hydrodynamic focusing can be adapted to align the fibres with their axes parallel to the flow of gas through the sensing volume so that the effect of particle orientation is minimized, for example as described in U.S. Pat. No. 4,027,162. In this patent there is described a technique for monitoring fibre aspect ratio involving the simultaneous monitoring of radiation scattered both perpendicular to the axis of the fibre and along the axis of the fibre. The ratio of the two intensities is taken as a measure of the aspect ratio of the fibre. The sum of the two intensities is taken as a measure of the absolute size, but the physical significance of this in relation to a fibrous particle is unclear. Since it is not a ratio of intensities, this sum is also sensitive to fibre refractive index and is subject to errors due to the particle passing through the edges of the illuminating beam where the intensity is less, as explained. Further, rigorous treatment of the theory of scattering by cylindrical fibres shows that the assumption that the aspect ratio of a fibre is proportional to the ratio of the scattered intensities perpendicular to and aligned with the fibre axis is only valid over a limited range of diameters, and it is necessary to apply a correction dependent on the absolute size of the fibre. This is clearly unsatisfactory when there is no independent method of determining the absolute size.

When airborne fibres are monitored in connection with the risk to health, only those fibres within a certain size range which are capable of entering and being deposited in the lung, i.e. respirable fibres, should be considered. Consequently it is sometimes thought that the aerodynamic size of a particle is the most useful indicator of particle size. The aerodynamic size of a spherical particle of unit density is taken as equivalent to its physical size, and for an irregularly shaped particle of a different density, the aerodynamic size is taken to be that of a unit density sphere having the same aerodynamic behaviour as the particle in question. Aerodynamic size is usually measured by measuring the velocity of the particle in a known flow field, for example by measuring its transit time between two laser beams, as described by J. Wu in Applied Optics, 177, vol. 16 p. 596- and W. G. Eisert and M. Nezel in Rev. Sci. Instr. 1978, vol.49 p. 1617. Detection of the passage of the particle may be achieved by detecting the dip in intensity of a beam as the particle passes through it, as described by Wu, or by monitoring the total light scattered by the particle as it passes through a beam, which is the method used in a commercially available instrument (TSI Inc, 500, Cardigan Road, St. Paul, MN, USA). Obviously, however, an aerodynamic sizing instrument cannot estimate aspect ratio. In the cell sizing instrument described by Eisert and Nezel, a system of hydrodynamic focusing is used to align the cells before passage through the beams, and further size information is obtained from scattering of light by passage of the cell through one of the beams. However, the scattering measurements proposed in this paper resemble the multiple ratio single particle scattering system according to Hirleman and described earlier, and no provision is made for estimating the aspect ratio of the fibre from the scattered radiation. Instead, the length of the fibre is estimated from the time of transit through one of the beams, and the scattering is limited to multiple angle scattering in a direction perpendicular to the particle axis. Consequently the fibre length measurement is determined only by its aerodynamic properties and a true aspect ratio cannot be obtained.

It is an object of the present invention to provide an instrument utilizing optical techniques which is capable of measuring the length and diameter of fibrous particles by optical means, which is insensitive to the refractive index of the particles and the intensity or uniformity of the source of illumination, and which is capable of unambiguous measurements even without calibration. It is a further object to provide an instrument which is capable of determining absolute size and aspect ratio of fibres together with their aerodynamic size. It is a yet further object to provide a fibre sizing instrument particularly suitable for the detection and estimation of asbestos fibres of the size range thought to be a danger to health.

In accordance with these objectives, there is provided apparatus for determining the size of fibrous particles, said apparatus comprising:

(1) means for generating at least one beam of radiation passing through a sensing volume;

(2) means for aligning said fibrous particles and passing them in single file along an axis intersecting said beam in said sensing volume;

(3) first, second, and third radiation detecting means, each having an output substantially proportional to the intensity of the radiation falling on it, respectively disposed to receive first, second and third portions of radiation scattered by said fibrous particles in near forward directions;

said first portion comprising radiation scattered within a first range of angles to said beam and passing through a first area on a plane perpendicularly disposed to said beam, said first area including the orthogonal projection of said axis on said plane;

said second portion comprising radiation scattered within a second range of angles to said beam and passing through a second area on said plane which includes the perpendicular in said plane to said orthogonal projection;

said third portion comprising radiation scattered within a third range of angles to said beam and passing through a third area on said plane which includes the perpendicular in said plane to said orthogonal projection, the angles included in said third range being greater than those included in said second range; and (4) means for combining the outputs of said first, second, and third radiation detecting means to obtain information on the size and shape of said fibrous particles.

Preferably, the means for combining comprises first means for determining the ratio of the outputs of said first and said second detecting means, second means for determining the ratio of the outputs of said second and said third detecting means, and third means for combining the ratios determined by the first and second means to obtain both the length and diameter of the fibrous particles. The output of the second means gives the diameter of the particle, substantially independently of the length, and the length of the particle can be obtained from the output of the first means once the diameter is known. In this way, accurate determinations of both length and diameter can be made.

Preferably also the means for generating the beam of radiation comprises a laser, for example a HeNe laser or solid state semiconductor laser. A spatial filter may be positioned after the laser source in order to provide a more uniform illumination of the sensing volume.

The means for aligning the particles preferably comprises a particle orienter which comprises a conduit of decreasing cross-section through which the fibrous particles flow under the influence of a stream of gas. This device exerts a hydrodynamic focusing effect and serves to define the sensing volume. Other methods of aligning the fibres, for example an electrostatic field, may alternatively be used. Preferably each of the radiation detecting means comprises a photomultiplier, or a photodiode.

Preferably the first area comprises two substantially indentical rectangles disposed on the plane one on each side of the point where the beam intersects the plane and so that the orthogonal projection bisects two opposite sides of each rectangle. The length of the rectangles (that is, measured along the sides which are not so bisected), is selected so that the first detecting means receives only scattered radiation falling within the first range of angles to the beam, and the width according to the considerations outlined below. Similarly, the second area preferably comprises two substantially identical rectangles disposed one on each side of the point of intersection of the beam with the plane and so that the perpendicular to the orthogonal projection bisects two opposite sides of each rectangle. The lengths and positions of these rectangles along the perpendicular to the orthogonal projection of the axis is selected so that the second detecting means receives only radiation scattered within the second range of angles. The third area also comprises two rectangles disposed along the perpendicular to the orthogonal projection whose length is selected to ensure that only radiation scattered in the third range of angles reaches the third detecting means. Therefore, the rectangles comprising the third area are disposed along the same axis as those comprising the second area, but because the angles comprising the third range are greater than those comprising the second range, the third area rectangles are situated further away from the point of intersection than are the second area rectangles.

The second and third ranges of angles are preferably chosen to be similar to the ranges of angles used in a conventional two-angle forward scatter particle detector. Ranges of 2°–5°, and 5°–10°, respectively, are suitable for asbestos fibres. The first range of angles is then selected to yield a convenient range of intensity ratios for the aspect ratio of the fibres to be determined. Typically, the first range of angles may also be 2°–5° for asbestos fibres.

The width of each of the rectangles comprising the second and third areas should be as great as possible to achieve maximum sensitivity, but the maximum usable width is limited by the effect of fibre length. The intensity of scattered radiation falling on the second and third detecting means in fact varies with the length of the fibres by an amount that varies non-linearly with fibre length. The ratio of the outputs of the second and third detecting means is used to determine the diameter of the fibre, and the inventors have found that this ratio remains substantially independent of the length of fibres up to a certain maximum length dependent on the width of the second and third area rectangles. The width must therefore be chosen as a compromise between a restricted width which results in the diameter determination being substantially independent of length up to a chosen maximum value of length, and the maximum possible width which gives the greatest sensitivity.

Thus a further preferred form of the invention comprises apparatus as defined above in which the width of the rectangles comprising said second and third areas, measured along the sides which are bisected by said perpendicular to the orthogonal projection, are chosen to be such that the ratio of the outputs of said second and third detecting means remains substantially independent of the length of said fibrous particles up to a chosen maximum length.

In the case of asbestos fibres up to 100 micron long, the width of the rectangles is selected so that it is not greater than that of a 2° sector of a circle drawn on the plane centered at its point of intersection with the beam and passing through the outermost part of each rectangle.

The fibre length is determined from the ratio of the outputs of the first and second detecting means, once the fibre diameter has been found from the ratio of the outputs of the second and third detecting means. The outputs of both the first and second detecting means respectively vary with the first and second ranges of angles in a way which depends non-linearly on the fibre diameter. Consequently the ratio of the outputs of the first and second detecting means is a function of both the length and diameter of the fibres. The effect of diameter on the output of the first detecting means is reduced by limiting the width of the rectangles comprising the first area (typically to correspond to a 2° sector of the circle defined above), but the effect on the second detecting means is unavoidable (it is of course used to determine the diameter of the particle). As a result, the determination of the fibre length requires both the ratio of the outputs of the first and second detecting means and a knowledge of the fibre diameter, which is determined in the present invention from the ratio of the outputs of the second and third detecting means. It is the absence of this independent measure of fibre diameter which limits the accuracy of the prior two-detector method described in U.S. Pat. No. 4,027,162.

In an alternative embodiment, said first, second, and third areas may each comprise at least part of two sectors of a circle disposed on a plane perpendicular to said beam and centered on the point of intersection of said beam with said plane, said at least part sectors being further disposed so that those comprising said first area are bisected by said orthogonal projection, and those comprising said second and third areas are bisected by the perpendicular to said orthogonal projection.

Preferably, the angles of the sectors are limited to correspond with those used to define the extent of the rectangles in the previously described embodiment, thereby achieving the same advantages obtained by so limiting the extent of the rectangles.

A variety of optical methods can be used to separate the scattered radiation into the required components and direct these components into the detecting means. A preferred form of the invention comprises apparatus as defined above further comprising:
(1) trapping means disposed in the path of the beam after passing through the sensing volume and adapted to absorb any unscattered radiation passing through said sensing volume;
(2) first reflecting means disposed in the path of the scattered radiation beyond said trapping means, said reflecting means intercepting a central portion of said scattered radiation and reflecting it along a direction remote from that of the scattered radiation which passes around said reflecting means, said reflecting means being dimensioned to intercept only that radiation lying within said first and second ranges of angles to said beam;

(3) masking means, disposed in the path of the scattered radiation which passes around said first reflecting means, and adapted to transmit to said third detecting means scattered radiation lying with said third range of angles and within said third area;

(4) partial reflecting means, disposed in the path of scattered radiation reflected by said first reflecting means, and adapted to:
 (a) pass radiation scattered within said second range of angles and said second area into said second detecting means, and
 (b) pass radiation scattered within said first range of angles and said first area into said first detecting means.

The trapping means may comprise a hollow cylinder closed at one end remote from the radiation source and coated with a radiation absorbing material, or a small elliptical plane mirror, inclined at an angle to the beam so that it presents a circular aperture when viewed from the sensing volume, which reflects the unscattered radiation into a more efficient trap such as a Rayleigh horn. In either case the trap (or mirror) is dimensioned so that radiation scattered at angles greater than the minimum to be detected passes around it.

The first reflecting means, comprising either a small mirror or prism, is placed in the path of the scattered radiation and is dimensioned to intercept radiation lying within the first and second ranges of angles, which it reflects away from the remaining scattered radiation, preferably at 90° to the original direction of the beam. The wide angle scattered radiation which lies within the third range of angles to the beam passes into the third detecting means via a masking means to restrict it to the third area and preferably via a lens to obviate the need for a wide aperture detector.

The narrow angle scattered radiation, reflected away from the direction of the beam by the first reflecting means, is further divided into the required two components by a partial reflecting means. The most suitable form of this comprises a part-silvered quadrant mirror, i.e. a plane mirror divided into four 90° sectors silvered only on two opposite sectors. This is disposed with a quadrant boundary at 45° to the axis of the fibres as it would appear in the narrow angle scattered beam in the absence of the radiation trap, so that light scattered up to ±45° to this axis is reflected into one detector and light scattered at ±45° to the perpendicular to the fibre axis is transmitted to the other detector (or v.v.). Although the detectors may be situated to directly receive the scattered radiation via a suitable optical arrangement, it is also within the scope of the invention to transmit the separated scattered components to the detectors by means of fibre optical light guides. This allows the detectors to be placed in any convenient location.

Masks are fitted in front of each detector, or at some other convenient place in the optical system, in order to accurately define the first, second, and third areas. Lenses are preferably used to focus the scattered radiation passing through the masks on to each detector. The masks can be arranged to transmit radiation scattered at any desired range of angles and within any desired area, and the choice is dependent on the factors previously discussed, especially the size of the fibres to be detected. For fibres of less than 5 micron diameter and between 5 micron and 100 micron in length, the most suitable scattering angle ranges are from 2° to 5° and 5° to 10° for the second and third ranges of angles, respectively, and from 2° to 5° for the first range of angles. The 2° lower limit to set by the dimensions of the radiation trapping means. The first, second, and third areas preferably each comprise two rectangles, the length and width of which are determined as previously described. These dimensions and ranges of angles allow an accurate and unambiguous determination of fibre diameter from the scattering in the range of interest and an accurate measure of aspect ratio according to the principle outlined in U.S. Pat. No. 4,027,162.

According to another aspect of the invention there is provided apparatus for determining the diameter of fibrous particles comprising:

(1) means for generating at least one beam of radiation passing through a sensing volume;

(2) means for aligning said fibrous particles and passing them in single file along an axis intersecting said beam in said sensing volume; and (3) first and second radiation detecting means, each having an output substantially proportional to the intensity of radiation incident upon it, respectively disposed to receive first and second portions of the radiation scattered in near forward directions by said fibrous particles;

said first portion comprising radiation scattered within a first range of angles to said beam and passing through a first area on a plane perpendicularly disposed to said beam, said first area including the perpendicular to the orthogonal projection of said axis on said plane;

said second portion comprising radiation scattered within a second range of angles to said beam and passing through a second area on said plane, said second area including the perpendicular to the orthogonal projection of said axis on said plane and the angles included in said second range being greater than those included in said first range;

wherein the extent of said first and second areas in a direction perpendicular to the orthogonal projection is limited to ensure that the ratio of the outputs of said first and second detecting means is substantially independent of the length of said fibrous particles up to a selected maximum length.

It will be appreciated that apparatus constructed in this way is similar to that previously described with the omission of one of the detecting means which was used to determine the aspect ratio of the fibrous particles. Thus by use of this two detector version of the invention, the accuracy of a conventional two-angle forward scatter particle sizer can be improved so that the diameter determination is substantially independent of fibre length by restriction of the scattered radiation to the first and second areas as described. In a conventional particle sizer based on this principle, such a restriction is not used, and usually the whole of the radiation scattered within the appropriate angular range is transmitted to the detectors. This results in the instrument giving incorrect results when used with fibrous particles because of the effect of length, described previously.

Details of the construction of the two-detector version of the invention are similar to the embodiments previously described with the omission of the first detector and its related optical components.

Any of the forms of the invention described above may further comprise means for generating at least two beams of radiation passing through said sensing volume, said beams being disposed so that radiation scattered from each beam by a fibre passing through it is received by at least one of said radiation detecting means, and means for determining the time between the arrival at that detecting means of radiation scattered by the passage of a fibre through one beam and the time of arrival of radiation scattered by the passage of said fibre through another of said beams. In this way, assuming that a hydrodynamic focusing device is used to align the fibres and pass them through the beams in single file, and with a knowledge of the flow rate of the fluid through it, it is possible to estimate the aerodynamic size of the fibre, preferably after calibration of the apparatus with particles of known size.

Preferably two collimated beams are used and the two or three radiation detectors are all arranged to receive scattered radiation from both beams, although the aerodynamic size can be determined from the signals on just one of them. This embodiment is easily achieved, if the beams are parallel and are spaced about 1 mm apart along the axis of fibre travel, without any modification of the optical system used for a single incident beam instrument. As the fibres of interest will not generally exceed 100 micron in length, they will pass completely through the first beam before entering the second beam, so that the signal at each detector consists of two identical portions displaced in time by an interval corresponding to the time taken for the fibre to travel between the two beams. The optical length and diameter of the fibre are simultaneously obtained by the method described previously. An additional advantage of this feature is that the number of false signals due to stray light, or more than one fibre passing through the sensing volume in a given instant, can be reduced by accepting only those signals that are duplicated on all three detectors within the expected time window. Any conventional type of beam splitter, disposed immediately after the radiation source, can be used to produce the two parallel beams.

In all the versions of the invention so far described, the outputs from the two or three detectors can be treated by suitable analogue electronics in order to derive the ratios necessary to give the length and diameter of the particles. Preferably, however, analogue-to-digital converters are connected to the detectors and the resultant digital signals, representative of the intensity of the radiation reaching the detectors, are processed by a digital computer or microprocessor. Although in some cases, calibration is not strictly necessary to obtain the length and diameter, the accuracy of the instrument can be improved by calibration with fibres of known size. Clearly, the instruments can also be used to provide a count of the number of fibres passing through them in a known volume of air, and the internal computer or microprocessor can be programmed to recognize those particles having lengths and diameters in the range likely to endanger health. Thus the instrument can be made to provide a direct measure of the number of dangerous fibres present in a sample and is therefore particularly suitable for the monitoring of atmospheres containing asbestos particles.

Examples of the invention will now be described in greater detail with reference to the accompanying drawings in which.

Figure 1:
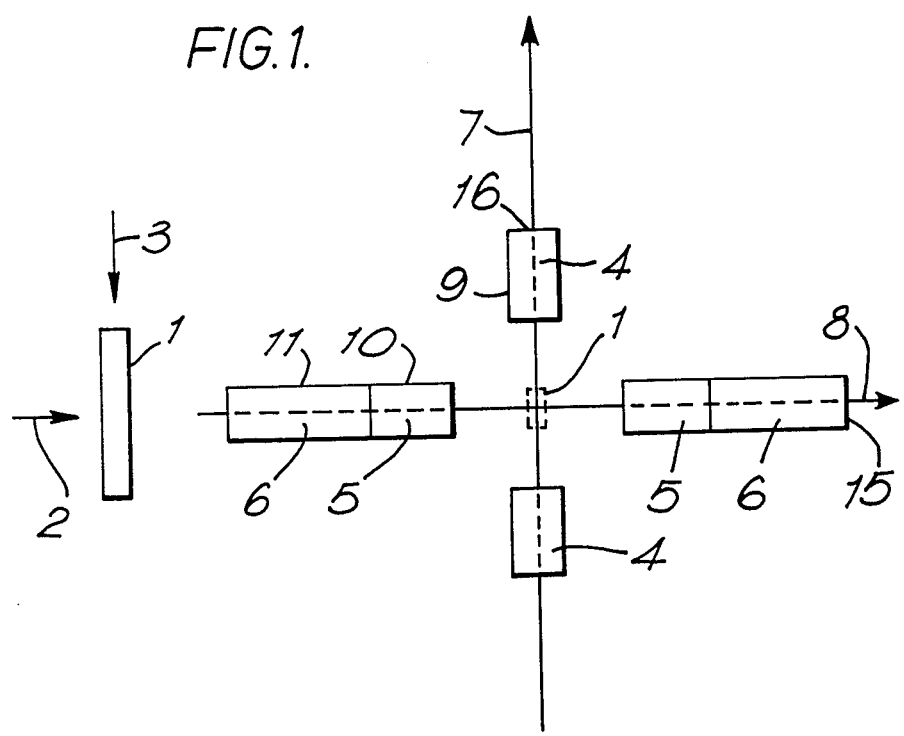
FIG. 1 is an explanatory diagram illustrating the areas and ranges of angles in which scattered radiation is accepted by the detectors in the case when the areas are rectangular.

Referring first to FIG. 1, an aligned fibre 1 is shown travelling through a beam of radiation 2 (usually laser light) in a direction 3 aligned with its axis. Radiation scattered by the fibre as it passes through the beam is detected in the rectangular areas 4, 5 and 6 shown in the righthand part of FIG. 1 which is a section through the beam of scattered radiation drawn in a plane perpendicular to beam 2 so that axis 7 is an orthogonal projection of the axis of the particle travel (3) on the plane, and axis 8 is a perpendicular in the plane to axis 7. Rectangles 4 comprise the first area in which radiation scattered within the first range of angles (defined by the length of side 9 of the rectangles) is accepted and transmitted to the first detecting means. Similarly, the pairs of rectangles 5 and 6 respectively comprise the second and third areas, so that the lengths of sides 10 of rectangles 5 and sides 11 of rectangles 6 respectively define the second and third ranges of angles.

Radiation falling outside rectangles 4, 5 or 6 is not detected, and the unscattered radiation which would be centered on the intersection of axes 7 and 8 is removed by a light trap. As explained, this defines the lower limit of the angular ranges corresponding to rectangles 4 and 5. The lengths of sides 9, 10 and 11 are selected according to the type of fibres to be monitored. Typically, for asbestos fibres, they should be selected so that rectangles 4 and 5 extend to collect radiation scattered from 2° to 5° relative to beam 2, and rectangles 6 from 5° to 10°.

Figure 6:
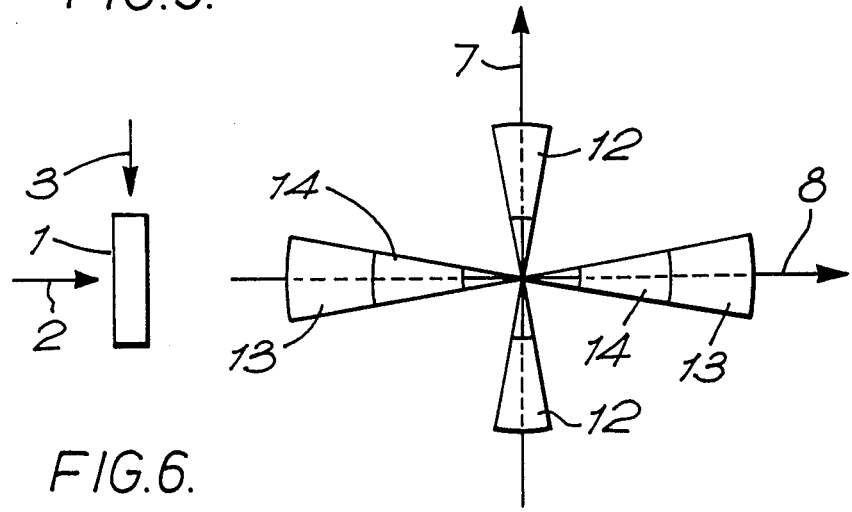
FIG. 6 is an explanatory diagram illustrating the areas and ranges of angles of scattered radiation accepted by the detectors in the case when the areas are sector shaped.

FIG. 6 is similar to FIG. 1 but shows the first, second, and third areas for an embodiment in which these are sector shaped. Sectors 12 comprise the first area, and sectors 14 and 13 comprise the second and third areas, respectively. The lengths of the sectors correspond to the lengths of sides 9, 10 and 11 in FIG. 1.

The widths of rectangles 4, 5 and 6, or the included angles of sectors 12, 13 and 14, are selected in the manner previously described. The width of side 15 (FIG. 1) should be equal to the chord drawn at the outer edge of sector 13 (FIG. 6), which is located the same distance from the origin of the diagram as side 15. Similarly, side 16 should be equal to the chord at the outermost boundary of sector 12. However, in the FIG. 1 embodiment, rectangle 5 has the same width (side 15) as rectangle 6, whilst in the FIG. 6 embodiment, sector 14 has a shorter chord length than sector 13. In practice this results in the FIG. 1 embodiment having greater sensitivity than the FIG. 6 embodiment.

Figure 2:
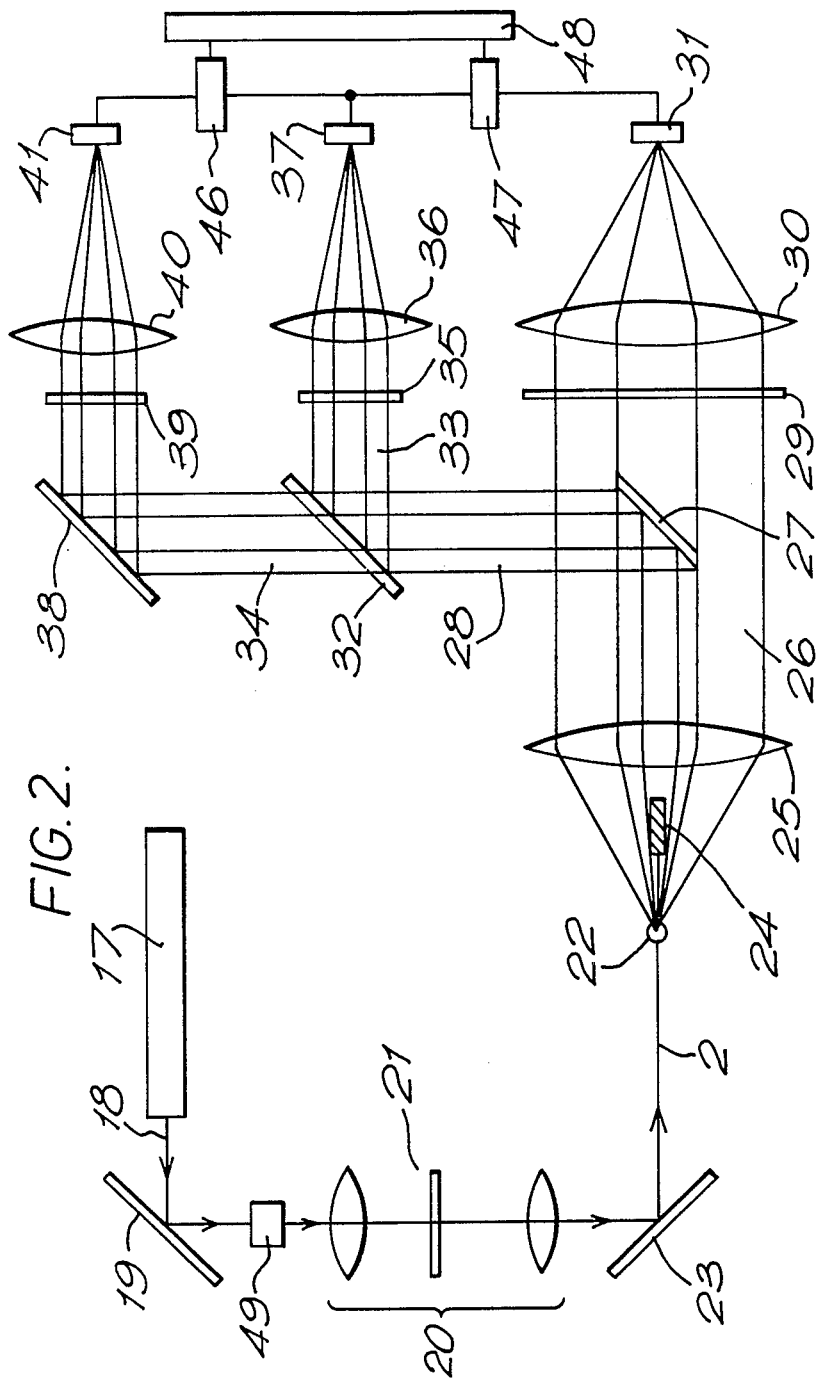
FIG. 2 is a schematic plan view of a preferred embodiment of apparatus according to the invention.

FIG. 2 shows a typical layout of an instrument constructed according to the invention. A low power HeNe laser 17 generates a beam 18 which is reflected by plane mirror 19 into telescope 20. The purpose of telescope 20 is to reduce the beam diameter to about 100 micron. A spatial filter 21 may also be incorporated to improve the uniformity of the output beam 2, which is reflected into sensing volume 22 by plane mirror 23. Sensing volume 22 is defined as the common volume of beam 2 and the area through which the aligned fibres 1 pass, and should be as small as possible to minimize the chance of two or more fibres being present in the volume simultaneously.

Alternatively, telescope 20 may be omitted, and replaced with a single lens (not shown) which is adapted to focus beam 2 into sensing volume 22.

A beam stop or light trap 24 absorbs any unscattered light from beam 2 so that only scattered light enters lens 25. It also determines the minimum angle of scattered light which reaches the detectors. The trap 24 may comprise a hollow cylinder closed at one end remote from the radiation source and coated with a radiation absorbing material, or a small elliptical plane mirror, inclined at an angle to the beam so that it presents a circular aperture when viewed from the sensing volume, which reflects the unscattered radiation into a more efficient trap such as a Rayleigh horn. The diameter of lens 25 must be sufficient to accept the widest scatter angles which are to be detected. Lens 25 produces a substantially parallel beam of scattered radiation 26. A plane mirror 27 (the first reflecting means), intercepts the central part of beam 26 and produces beam 28 which contains the radiation scattered within rectangles 4 and 5 of FIG. 1 (or sectors 12 and 14 of FIG. 6). The wider angle scattered radiation, comprising that scattered in rectangles 6 or sectors 13, passes around mirror 27 and through mask 29 into lens 30 which focuses it on to detecting means 31, typically a photomultiplier. Mirror 27 is preferably elliptical so that it presents a circular aperture to beam 26, but other shapes are also possible, e.g., a small rectangular mirror could be used providing that the width of the rectangles or sectors is not too great.

Beam 28 is further divided by a part silvered mirror 32 (described below) into a beam 33 which contains the scattered radiation falling within rectangles 5 or sectors 14, and beam 34 containing scattered radiation falling within rectangles 4 or sectors 12. Beam 33 passes through mask 35 and lens 36 to detector 37, whilst beam 34 is reflected by plane mirror 38 through mask 39 and lens 40 to detector 41. Detectors 37 and 41 are preferably photomultipliers. Masks 29, 35 and 39 are shaped to allow only radiation falling within the sectors or rectangles to reach the detectors.

Figure 3:
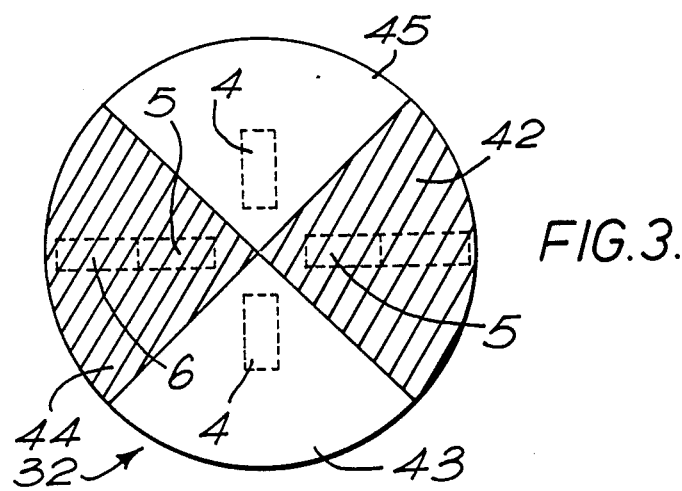
FIG. 3 is a view of a partially silvered mirror utilized in the embodiment shown in FIG. 2.

Part silvered mirror 32, illustrated in FIG. 3, comprises a small plane mirror divided into four quadrants 42–45 of which two oppositely disposed sectors 42 and 44 are silvered. It is positioned in beam 28 with a boundary between its quadrants at 45° to the axis of the fibre as it would appear in beam 28, so that light scattered perpendicular to the fibre axis falling within rectangles 5 is reflected to form beam 33 by sectors 42 and 44, whilst light scattered along the fibre axis is transmitted to form beam 34 by transparent sectors 43 and 45.

It will be appreciated that mirrors 19, 23 and 38 are provided simply to allow a compact instrument to be constructed but if size is not an important consideration it is preferable to omit them, repositioning the detector 41, laser 17 and telescope 20 accordingly. In this way the number of optical elements in the path of the light is minimised so that the effect of vibration on the performance of the instrument can be reduced.

The signals from detectors 41, 37 and 31 are combined by dividers 46 and 47 to produce signals indicative of the fibre aspect ratio and diameter, respectively. The ratio signals are further combined in processor 48 which produces a display or recording of the dimensions of each fibre passing through the sensing volume 22. Processor 48 may also incorporate a counter to register the number of fibres detected in a given time. Preferably, dividers 46 and 47, and processor 48 comprise a suitably programmed digital computer, and analogue-to-digital converters are used to convert the signals from the detectors into digital values suitable for the computer.

Figure 4:
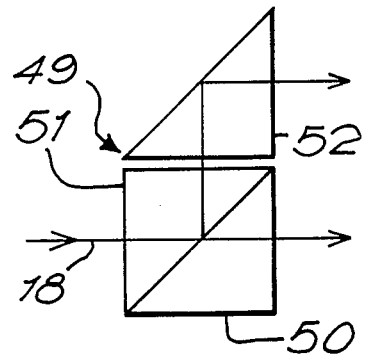
FIG. 4 illustrates a beam splitter suitable for use in an embodiment of the invention.

In order to adapt the instrument to provide a measure of aerodynamic size as well as optical size, a beamsplitter 49 is inserted in the path of the beam between mirror 19 and telescope 20 (FIG. 2). Beamsplitter 49, illustrated in FIG. 4, produces two beams disposed in two planes parallel to each other and perpendicular to the direction of travel of the fibres through sensing volume 22. The beams leaving the beamsplitter are spaced about 5 mm apart, so that after passing through telescope 20 they will be about 1 mm apart. Typically, beamsplitter 49 comprises three prisms 50, 51, 52 disposed as shown in FIG. 4. When two beams are provided, it is of course not possible to replace telescope 20 by a single lens as suggested above because the spatial separation of the beams will be destroyed.

The two beams leaving telescope 20 travel through the rest of the instrument in an identical way, so that two identical scatter signals are produced at each detector, displaced in time as the fibre travels through each beam in turn. The time interval can be measured by processor 48 and used to calculate the aerodynamic size of the fibre.

Figure 5:
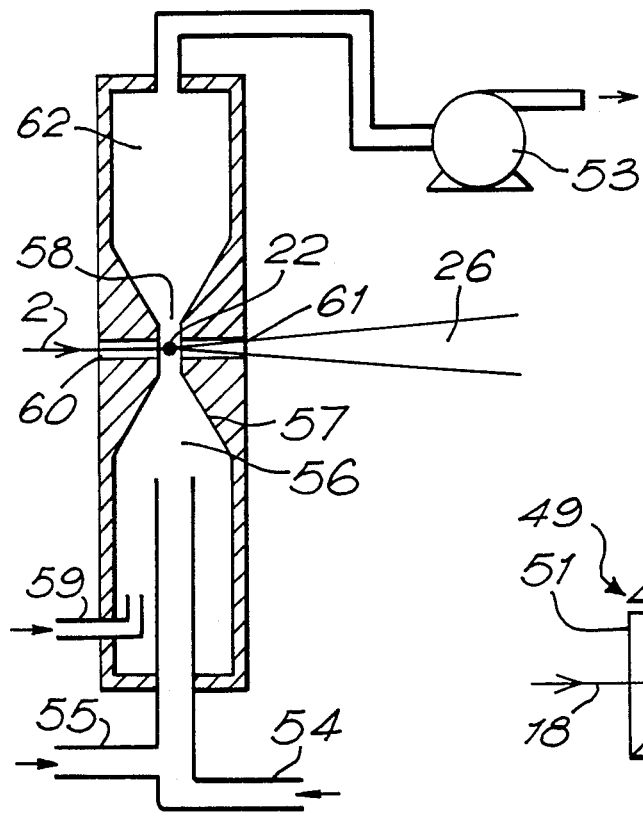
FIG. 5 shows a particle orienter suitable for use with the invention.

FIG. 5 shows a particle orienter suitable for use with the invention. It will be appreciated that such systems are well known in the art and the invention is not limited to use of an orienter of this type.

The fibre-laden sample fluid (usually atmospheric air) is drawn by means of vacuum pump 53 through inlet tube 54. If the air contains so many fibres that the concentration range of the instrument is exceeded, a flow of clean air may be added through branch pipe 55 in order to dilute the sample. Laminar flow is established in region 56, and hydrodynamic focusing is caused to occur by means of cone 57 so that the fibres are aligned with the direction of flow and pass in single file through sensing volume 22 inside narrow tube 58. A flow of clean air is added through inlet 59 so that a sheath of clean air surrounds the fibre-laden air in tube 58, preventing deposition of the fibres in the apparatus and improving the hydrodynamic focusing action. Beam 2 passes into the nozzle assembly through hole 60 and intercepts the fibre-laden air stream in sensing volume 22. The radiation scattered by the fibres emerges through hole 61. After crossing beam 2 the sheathed sample air passes into chamber 62, which is also fitted with a conical section to ensure laminar flow is maintained through tube 58. Exhaust vacuum pump 53 draws the sample air from chamber 62.

Clearly, various valves and flowmeters are required to control the operation of the orienter, but the disposition of these is conventional. The supply of clean air needed for the dilution of the sample and the production of the sheath can conveniently be derived from the outlet of pump 53 after filtration to remove the fibres. It is important that the added clean air has the same optical and chemical properties as the sample air containing the fibres if the apparatus is to operate correctly.

What is claimed is:

1. Apparatus for determining the size of fibrous particles, said apparatus comprising:

(1) means for generating at least one beam of radiation passing through a sensing volume;

(2) means for aligning said fibrous particles and passing them in single file along an axis intersecting said beam in said sensing volume;

(3) first, second, and third radiation detecting means, each having an output substantially proportional to the intensity of the radiation falling on it, respectively disposed to receive first, second and third portions of radiation scattered by said fibrous particles in near forward directions;

said first portion comprising radiation scattered within a first range of angles to said beam and passing through a first area on a plane perpendicularly disposed to said beam, said first area including the orthogonal projection of said axis on said plane;

said second portion comprising radiation scattered within a second range of angles to said beam and passing through a second area on said plane which includes the perpendicular in said plane to said orthogonal projection;

said third portion comprising radiation scattered within a third range of angles to said beam and passing through a third area on said plane which includes the perpendicular in said plane to said orthogonal projection, the angles included in said third range being greater than those included in said second range; and (4) means for combining the outputs of said first, second, and third radiation detecting means to obtain information on the size and shape of said fibrous particles.

2. Apparatus according to claim 1 in which said first area comprises two substantially identical rectangles disposed on said plane one on each side of the point where said beam intersects said plane and so that said orthogonal projection bisects two opposite sides comprising the width of each rectangle, said second area comprises two substantially identical rectangles disposed one on each side of the point of intersection of said beam with said plane and so that the perpendicular to said orthogonal projection bisects two opposite sides comprising the width of each rectangle, and said third area comprises two substantially identical rectangles disposed either side of the point of intersection of said beam with said plane and so that the perpendicular to said orthogonal projection bisects two opposite sides comprising the width of each rectangle.

3. Apparatus according to claim 1 in which said first, second, and third areas each comprise at least part of two sectors of a circle disposed on a plane perpendicular to said beam and centered on the point of intersection of said beam with said plane, said at least part sectors being further disposed so that those comprising said first area are bisected by said orthogonal projection, and those comprising said second and third areas are bisected by the perpendicular to said orthogonal projection.

4. Apparatus according to claim 2 in which the maximum widths of the rectangles comprising said second and third areas are limited to ensure that the ratio of the outputs of said second and third detecting means remains substantially independent of the length of said fibrous particles up to a chosen maximum length.

5. Apparatus according to claim 3 in which the maximum angles of the sectors comprising said second and third areas are limited to ensure that the ratio of the outputs of said second and third detecting means remains substantially independent of the length of said fibrous particles up to a chosen maximum length.

6. Apparatus according to claim 4, adapted for the determination of asbestos fibres up to 100 micron long, in which said first and second ranges of angles are 2° to 5°, said third range of angles to 5° to 10°, and in which the maximum width of each of said rectangles comprising each of said areas does not exceed the maximum width of a 2° sector of a circle drawn on said plane, said circle being centered at the point of intersection of said plane with said beam and passing through the outermost boundary of each area.

7. Apparatus according to claim 5, adapted for the determination of asbestos fibres up to 100 micron long, in which said first and second ranges of angles are 2° to 5°, said third range of angles is 5° to 10°, and in which the angle of each of the sectors comprising each of said areas does not exceed 2°.

8. Apparatus according to claim 1 further comprising:

(1) trapping means disposed in the path of the beam after passing through the sensing volume and adapted to absorb any unscattered radiation passing through said sensing volume;

(2) first reflecting means disposed in the path of the scattered radiation beyond said trapping means, said reflecting means intercepting a central portion of said scattered radiation and reflecting it along a direction remote from that of the scattered radiation which passes around said reflecting means, said reflecting means being dimensioned to intercept only that radiation lying within said first and second ranges of angles to said beam;

(3) masking means, disposed in the path of the scattered radiation which passes around said first reflecting means, and adapted to transmit to said third detecting means scattered radiation lying within said third range of angles and within said third area;

(4) partial reflecting means, disposed in the path of scattered radiation reflected by said first reflecting means, and adapted to:
 (a) pass radiation scattered within said second range of angles and said second area into said second detecting means, and
 (b) pass radiation scattered within said first range of angles and said first area into said first detecting means.

9. Apparatus according to claim 2 further comprising:

(1) trapping means disposed in the path of the beam after passing through the sensing volume and adapted to absorb any unscattered radiation passing through said sensing volume;

(2) first reflecting means disposed in the path of the scattered radiation beyond said trapping means, said reflecting means intercepting a central portion of said scattered radiation and reflecting it along a direction remote from that of the scattered radiation which passes around said reflecting means, said reflecting means being dimensioned to intercept only that radiation lying within said first and second ranges of angles to said beam;

(3) masking means, disposed in the path of the scattered radiation which passes around said first reflecting means, and adapted to transmit to said third detecting means scattered radiation lying within said third range of angles and within said third area;

(4) partial reflecting means, disposed in the path of scattered radiation reflected by said first reflecting means, and adapted to:
  (a) pass radiation scattered within said second range of angles and said second area into said second detecting means, and
  (b) pass radiation scattered within said first range of angles and said first area into said first detecting means.

10. Apparatus according to claim 3 further comprising:
  (1) trapping means disposed in the path of the beam after passing through the sensing volume and adapted to absorb any unscattered radiation passing through said sensing volume;
  (2) first reflecting means disposed in the path of the scattered radiation beyond said trapping means, said reflecting means intercepting a central portion of said scattered radiation and reflecting it along a direction remote from that of the scattered radiation which passes around said reflecting means, said reflecting means being dimensioned to intercept only that radiation lying within said first and second ranges of angles to said beam;
  (3) masking means, disposed in the path of the scattered radiation which passes around said first reflecting means, and adapted to transmit to said third detecting means scattered radiation lying within said third range of angles and within said third area;
  (4) partial reflecting means, disposed in the path of scattered radiation reflected by said first reflecting means, and adapted to:
    (a) pass radiation scattered within said second range of angles and said second area into said second detecting means, and
    (b) pass radiation scattered within said first range of angles and said first area into said first detecting means.

11. Apparatus for determining the diameter of fibrous particles comprising:
  (1) means for generating at least one beam of radiation passing through a sensing volume;
  (2) means for aligning said fibrous particles and passing them in single file along an axis intersecting said beam in said sensing volume; and
  (3) first and second radiation detecting means, each having an output substantially proportional to the intensity of radiation incident upon it, respectively disposed to receive first and second portions of the radiation scattered in near forward directions by said fibrous particles;

said first portion comprising radiation scattered within a first range of angles to said beam and passing through a first area on a plane perpendicularly disposed to said beam, said first area including the perpendicular to the orthogonal projection of said axis on said plane;
  said second portion comprising radiation scattered within a second range of angles to said beam and passing through a second area on said plane, said second area including the perpendicular to the orthogonal projection of said axis on said plane and the angles included in said second range being greater than those included in said first range; the improvement comprising limiting the extent of said first and second areas in a direction perpendicular to said perpendicular to the orthogonal projection to ensure that the ratio of the outputs of said first and second detecting means is substantially independent of the length of said fibrous particles up to a selected maximum length.

12. Apparatus according to claim 11 in which said first and second areas each comprise two substantially identical rectangles disposed on said plane one on each side of the point where said beam intersects said plane and so that the perpendicular to said orthogonal projection bisects two opposite sides comprising the width of said rectangles.

13. Apparatus according to claim 11 in which said first and second areas each comprise at least part of two sectors of a circle disposed on a plane perpendicular to said beam and centered on the point of intersection of said beam with said plane, and disposed so that they are bisected by the perpendicular to said orthogonal projection.

14. Apparatus according to claim 12 adapted for the determination of the diameter of asbestos fibres up to 100 micron long, in which said first range of angles is 2° to 5°, said second range of angles is 5° to 10°, and in which the maximum width of each of said rectangles comprising each of said areas does not exceed the maximum width of a 2° sector of a circle drawn on said plane, said circle being centered at the point of intersection of said plane with said beam and passing through the outermost boundary of each said area.

15. Apparatus according to claim 13 adapted for the determination of the diameter of asbestos fibres up to 100 micron long, in which said first range of angles is 2° to 5°, said second range of angles is 5° to 10°, and in which the maximum angle of each of said sectors does not exceed 2°.

16. Apparatus according to claim 1 further comprising means for generating at least two beams of radiation passing through said sensing volume, said beams being disposed so that radiation scattered from each beam by a fibrous particle passing through it is received by at least one said detecting means, and means for determining the time interval between the arrival at that detecting means of radiation scattered by said particle passing through one beam and the arrival of radiation scattered by said particle passing through another of said beams.

17. Apparatus according to claim 8 further comprising means for generating at least two beams of radiation passing through said sensing volume, said beams being disposed so that radiation scattered from each beam by a fibrous particle passing through it is received by at least one said detecting means, and means for determining the time interval between the arrival at that detecting means of radiation scattered by said particle passing through one beam and the arrival of radiation scattered by said particle passing through another of said beams.

18. Apparatus according to claim 11 further comprising means for generating at least two beams of radiation passing through said sensing volume, said beams being disposed so that radiation scattered from each beam by a fibrous particle passing through it is received by at least one said detecting means, and means for determining the time interval between the arrival at that detecting means of radiation scattered by said particle passing through one beam and the arrival of radiation scattered by said particle passing through another of said beams.

19. Apparatus according to claim 1 in which said means for generating comprises at least one laser and said detecting means comprise photomultipliers.

20. Apparatus according to claim 2 in which said means for generating comprises at least one laser and said detecting means comprise photomultipliers.

21. Apparatus according to claim 3 in which said means for generating comprises at least one laser and said detecting means comprise photomultipliers.

22. Apparatus according to claim 8 in which said means for generating comprises at least one laser and said detecting means comprise photomultipliers.

23. Apparatus according to claim 11 in which said means for generating comprises at least one laser and said detecting means comprise photomultipliers.

* * * * *